(12) United States Patent
Birtwhistle et al.

(10) Patent No.: US 8,819,849 B2
(45) Date of Patent: Aug. 26, 2014

(54) CUSTOMER SUPPORT ACCOUNT WITH RESTRICTED PATIENT DATA ACCESS

(75) Inventors: Daniel P. Birtwhistle, Fishers, IN (US); Robert E. Reinke, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 115 days.

(21) Appl. No.: 13/400,313

(22) Filed: Feb. 20, 2012

(65) Prior Publication Data

US 2013/0167249 A1 Jun. 27, 2013

Related U.S. Application Data

(60) Provisional application No. 61/579,307, filed on Dec. 22, 2011.

(51) Int. Cl.
*G06F 7/04* (2006.01)
*G06F 17/30* (2006.01)
*H04N 7/16* (2011.01)

(52) U.S. Cl.
USPC .............. 726/28; 726/26; 726/30; 713/182

(58) Field of Classification Search
USPC ............................ 726/26–30; 713/182–186
See application file for complete search history.

(56) References Cited

U.S. PATENT DOCUMENTS

| 8,146,165 B2 * | 3/2012 | Manickam et al. ............ 726/26 |
| 2004/0139156 A1 * | 7/2004 | Matthews et al. ............ 709/204 |
| 2007/0061266 A1 | 3/2007 | Moore et al. |
| 2007/0095354 A1 * | 5/2007 | Churchill et al. ............ 128/897 |
| 2007/0300306 A1 * | 12/2007 | Hussain ............ 726/27 |
| 2008/0256399 A1 | 10/2008 | Erdosi et al. |
| 2009/0055904 A1 * | 2/2009 | Gomi et al. ............ 726/4 |
| 2009/0150825 A1 | 6/2009 | Yokoyama et al. |
| 2009/0164878 A1 | 6/2009 | Cottrille |
| 2009/0248680 A1 * | 10/2009 | Kalavade ............ 707/5 |
| 2010/0131551 A1 | 5/2010 | Benzaken et al. |
| 2010/0241844 A1 | 9/2010 | Hussain et al. |
| 2011/0202798 A1 * | 8/2011 | Vera et al. ............ 714/27 |

(Continued)

FOREIGN PATENT DOCUMENTS

| EP | 2375353 | 10/2011 |
| WO | WO2006104810 | 10/2006 |

OTHER PUBLICATIONS

45 Code of Federal Regulations, 164.52B—Accounting of Disclosures of Protected Health Information; revised as of Oct. 2, 2010.

(Continued)

*Primary Examiner* — Jeffrey Pwu
*Assistant Examiner* — Jayesh Jhaveri
(74) *Attorney, Agent, or Firm* — Roche Diagnostics Operations, Inc.

(57) ABSTRACT

A method for accessing a user's account by customer support without viewing the user's private data includes receiving, in an application module communicating with a web service, a request for authentication by a support person using a linked user-support login name. The method includes authenticating the user, authenticating the support person and retrieving a current session of the user as viewed by the user on an electronic screen of a processing device of the user. The method further includes dynamically redacting private data of the user from the user session to create a redacted user session, and delivering the redacted user session for display in an electronic screen of a processing device of the support person.

20 Claims, 3 Drawing Sheets

(56) References Cited

U.S. PATENT DOCUMENTS

| | | |
|---|---|---|
| 2012/0046972 A1 | 2/2012 | Tonti et al. |
| 2012/0066757 A1* | 3/2012 | Vysogorets et al. ............... 726/9 |
| 2012/0089860 A1* | 4/2012 | Zaifman et al. ................... 714/2 |
| 2013/0117830 A1* | 5/2013 | Erickson et al. ................... 726/6 |

OTHER PUBLICATIONS

"Citrix GoToAssist Corporate Security White Paper", www.citrixonlinecdn.com (2010).

\* cited by examiner

CUSTOMER SUPPORT ACCOUNT WITH RESTRICTED PATIENT DATA ACCESS

CROSS-REFERENCE TO RELATED APPLICATIONS

This application claims the benefit of U.S. Provisional Application No. 61/579,307, filed on Dec. 22, 2011. The entire disclosure of the above application is incorporated herein by reference.

FIELD

The present disclosure relates to a system and method for providing customer support by dynamically accessing a user's account that is modified to restrict access to private data of the user.

BACKGROUND

Title II of the Health Insurance Portability and Accountability Act (HIPAA) includes a Privacy Rule. The HIPAA Privacy Rule regulates the use and disclosure of certain information held by "covered entities" including health insurers, medical service providers and others that engage in certain transactions. The Privacy Rule establishes regulations for the use and disclosure of Protected Health Information (PHI) regarding health status, provision of health care, or payment for health care associated with an individual or patient. PHI covers, among other information, any part of an individual's medical record or payment history. A covered entity may disclose PHI to facilitate treatment, payment, or health care operation or if the covered entity has obtained authorization from the individual.

Additionally, when a covered entity discloses any PHI, it must make a reasonable effort to disclose only the minimum necessary information required to achieve its purpose. Increasingly, many patients, especially patients with chronic conditions that require daily management, such as diabetes, participate in health care management plans that include using software to manage, monitor, log, update and transfer data to a health management service or a participating health provider. Typically, a user (patient or health professional) interacts with software provided by the health management service or other health professional. The software can be in the form of an application or program which resides in a computer device (PC, laptop, tablet, smartphone or other hand held device) of the user or communicates with a web service of a health management service or provider by means of a web browser of the user. When an error occurs during the use of the application, the user can communicate by telephone or e-mail, or other digital communication with a support service. The support person that receives the call may not, however, be able to reproduce the error to determine the cause of the problem without seeing what the user sees and without tracing the user's actions. Permission to see private information of the user must be sought and saved in an audit log according to the PHI rule of HIPAA. Even when such permission is received, the experience may not be comfortable for the user and support member.

In the exemplary case of patients with diabetes, for example, diabetes is managed primarily by controlling the level of glucose in the bloodstream (bG). This level is dynamic and complex, and is affected by multiple factors including the amount and type of food consumed, and the amount of insulin (which mediates transport of glucose across cell membranes) in the blood. Blood glucose levels are also sensitive to exercise, sleep, stress, smoking, travel, illness, menses, and other psychological and lifestyle factors unique to individual patients. The dynamic nature of blood glucose and insulin, and all other factors affecting blood glucose, often require a person with diabetes to forecast blood glucose levels. Therefore, therapy in the form of insulin or oral medications, or both, can be timed to maintain blood glucose levels in an appropriate range.

Generally, management of diabetes is time-consuming for patients because of the need to consistently obtain reliable diagnostic information, follow prescribed therapy, and manage lifestyle on a daily basis. Diagnostic information, such blood glucose, is typically obtained from a capillary blood sample with a lancing device and is then measured with a handheld blood glucose meter. Interstitial glucose levels can be obtained from a continuous glucose sensor worn on the body. Prescribed therapies can include insulin, oral medications, or both. Insulin can be delivered with a syringe, an ambulatory infusion pump, an insulin patch or combinations thereof. With insulin therapy, determining the amount of insulin to be injected can require forecasting meal composition of fat, carbohydrates and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data acquired in a variety of ways: from medical devices, from personal healthcare devices, from patient recorded logs, from laboratory tests, and from healthcare professional recommendations. Medical devices include bG meters, continuous glucose monitors, ambulatory insulin infusion pumps, diabetes analysis software, and diabetes device configuration software. Each of these systems generates and/or manages large amounts of diagnostic and prescriptive data. Personal healthcare devices include weight scales, and blood pressure cuffs, exercise machines, thermometers, and weight management software. Patient recorded logs include information relating to meals, exercise and lifestyle. Lab test results include HbA1C, cholesterol, triglycerides, and glucose tolerance. Recommendations by healthcare professionals may include prescriptions, diets, test plans, and other information relating to the patient's treatment.

At the interaction of a patient or health professional with software used by the patient and health professional in the management of diabetes as describe above, software or other application errors can be encountered in association with files, forms or screen views that also include personal, medical or other health information of the patient that is protected by the Privacy Rule of HIPAA and referenced herein as private information.

The present teachings are directed to addressing this problem by enabling access by a support person to a user's account that is dynamically modified to restrict access to protected private data of the user.

SUMMARY

This section provides a general summary of the disclosure, and is not a comprehensive disclosure of its full scope or all of its features.

The present teachings provide a method for accessing a user's account by customer support without viewing the user's private data. In some embodiments, the method includes receiving, in an application module communicating with a web service, a request for authentication by a support person using a linked user-support login name. The method includes authenticating the user, authenticating the support person and retrieving a current session of the user as viewed by the user on an electronic screen of a processing device of the user. The method further includes dynamically redacting private data of the user from the user session to create a redacted user session, and delivering the redacted user session for display in an electronic screen of a processing device of the support person.

In some embodiments, the method includes receiving, in a health management module communicating with a web service, a request for authentication by a support person using the support person's password for the health management module and a login name that links the user login name and the support person's login name and includes a notification prefix. The method includes authenticating the user, authenticating the support person and retrieving a current session of the user as viewed by the user on an electronic screen of a processing device of the user. The method includes identifying in an electronic file of the current session of the user fields pre-tagged as private, dynamically redacting values of the pre-tagged fields to create a redacted electronic file for a redacted user session, sending the redacted electronic file to a support module of the web service, and displaying the redacted user session in an electronic screen of a processing device of the support person.

The present teachings also include a system for accessing a user's account by customer support without viewing the user's private data. The system includes a web service, a health management module communicating with the web service and accessible by a user having an account and authentication credentials with the web service, and a support module communicating with the web service and accessible by a support person having a support account and authentication credentials with the web service. The system also includes an authentication service communicating with the web service and programmed to (a) authenticate the user with the user's credentials, (b) authenticate the support person with the support person's credentials, and (c) authenticate the support person with linked user-support credentials for a limited access of the user's account. The system also includes a redaction module communicating with the authentication service and programmed to redact dynamically private data from a user's session with the web service and send the redacted user session to the support module for access by the support person, when the support person is authenticated with the linked user-support credentials.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
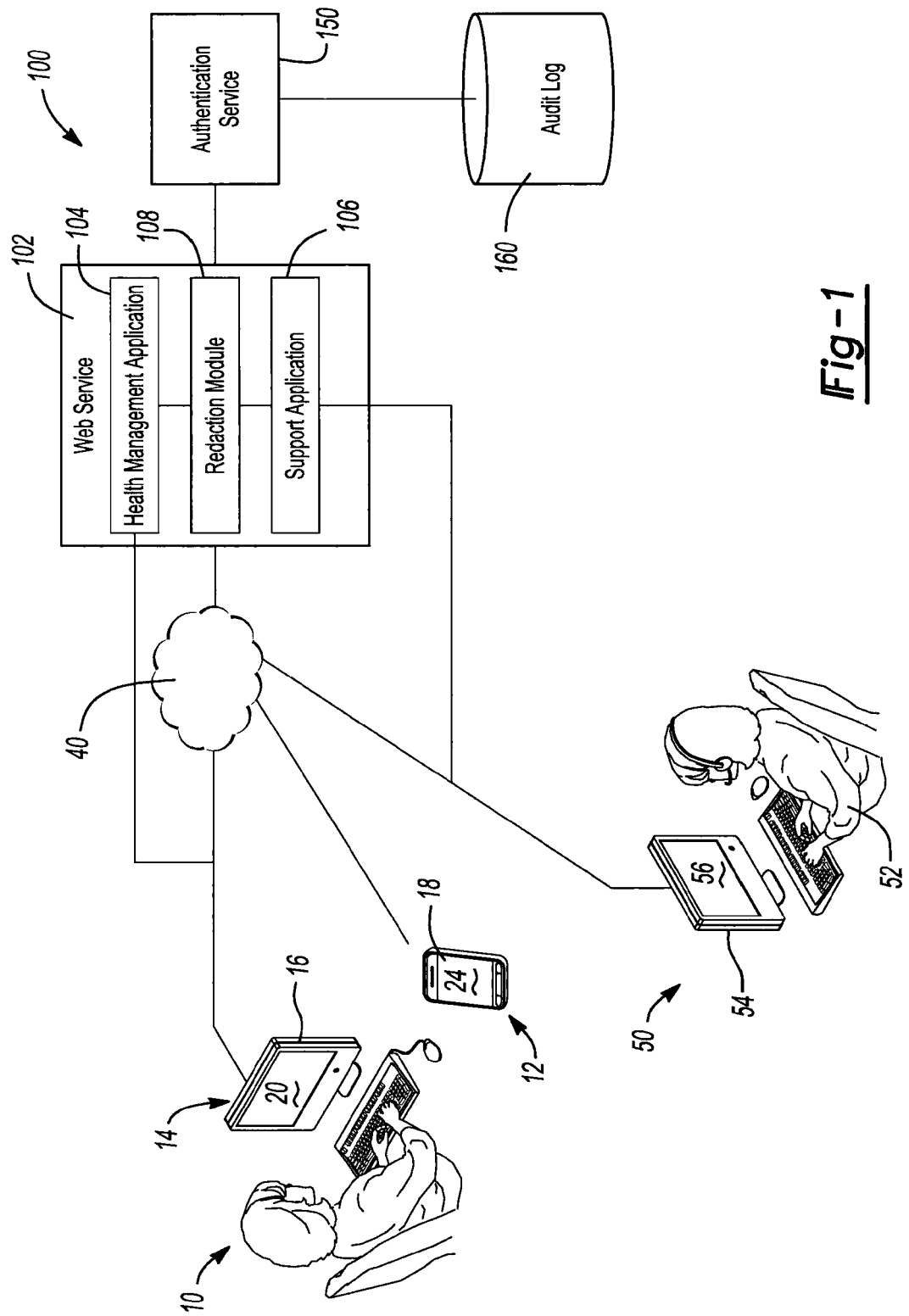
FIG. 1 illustrates an exemplary diagram of a system for customer support according to the present teachings.

The following description is merely illustrative in nature and is in no way intended to limit the disclosure, its application, or uses. For purposes of clarity, the same reference numbers will be used in the drawings to identify similar elements.

Referring to FIG. 1, a diagram for an exemplary system 100 for providing dynamic customer support with restricted access to the private data of a user is illustrated. For clarity, the system 100 is described in the context of health management, such as diabetes, but the present teachings are applicable to any other systems in which a user needs customer support for a computer-implemented application from a provider of the service for the application without having to share certain private information.

A user 10 can be either a person with diabetes or a health care provider that can interact with a web service 102 to access a health management application 104 (HMA). Persons with diabetes include persons with metabolic syndrome, pre-diabetes, type 1 diabetes, type 2 diabetes, gestational diabetes, and other types of diabetes and are collectively referred to as the patient herein. Healthcare providers for diabetes are diverse and include nurses, nurse practitioners, physicians, and endocrinologists and are collectively referred to as the clinician herein. Accordingly, the user 10 can be a patient or a clinician using the web service 102 and the health management application 104 for different purposes. For example, during a healthcare consultation, a patient typically shares with a clinician a variety of patient data including blood glucose measurements, continuous glucose monitor data, insulin infused, food and beverages consumption, exercise, and other lifestyle information. This patient data can be recorded manually on a patient diary or other tools such as an Accu-Chek® 360 View Blood Glucose Analysis System form or electronically on a handheld diabetes manager, such as the handheld diabetes manager 12, or electronically on personal computer (PC) 14 using diabetes analysis software, or electronically on a web-based diabetes analysis site or web service 102, or a combination of these means. The personal computer or computer processing device 14, as used herein, can be a desktop, laptop, tablet, smartphone or handheld processing device having any operating system, including operating systems by Microsoft Corporation (Windows and successors), by Apple Corporation (IOS and successors), by Linux or other operating systems, such as Android, webOS, etc. The personal computer 14 can include an electronic screen or display 20. The clinician will often obtain additional patient biomarker data such as measurements of HbA1C, cholesterol levels, triglycerides, blood pressure, and weight. The clinician can analyze the patient data using manual techniques, electronically using diabetes analysis software, or a web-based diabetes analysis site, such as the web service 102, the health management application 104 or a combination of these means. After analyzing the patient data along with the patient's adherence to the previously prescribed therapy, the clinician can decide whether to modify the therapy for the patient. In considering whether to modify the therapy, the clinician may need to balance the interests of the patient, the payer (not shown), and the clinician. Healthcare records systems such as Microsoft® HealthVault™ and Google™ Health can be used by the patient and clinician to exchange information via a communications network 40, such as the internet or web, communicating with the web service 102.

Accordingly, the user 10 (patient or clinician) may interact with a health management software (program or code) in the form of a HMA 104 that may reside in the user's PC 14 or in the web service 102, as shown in the exemplary illustration of FIG. 1, or both, or that may have sub-modules in both the PC 14 and web service 102 that can communicate (wired or wirelessly) via the internet or web or cellular network or other communications network 40. The user 10 may also connect the diabetes manager (or other portable device) 12 to the PC 14, wirelessly, by using a device reader or device dock or by USB connection for exchanging data, updating or installing software or other digital record management and transfer with either the same Health Management Application 104 or another local health management application (module or software) 16 residing in the user's PC 14. The diabetes manager 12 can include an electronic screen or display 24. In other embodiments, the diabetes manager 12 can communicate directly with the web service 102 for data transfer and use the health management application 104 at the web service 102 or locally with a corresponding software module or health management application 18. The diabetes manager 12 can be a handheld device that can include a bG meter and/or an insulin pump control device for a user 10 who is a patient. The diabetes manager 12 can also be a portable or handheld device used by a clinician to communicate with the patient, the patient's diabetes manager, clinical records of the patient's in the clinician's office and with the web service 102.

Figure 3:
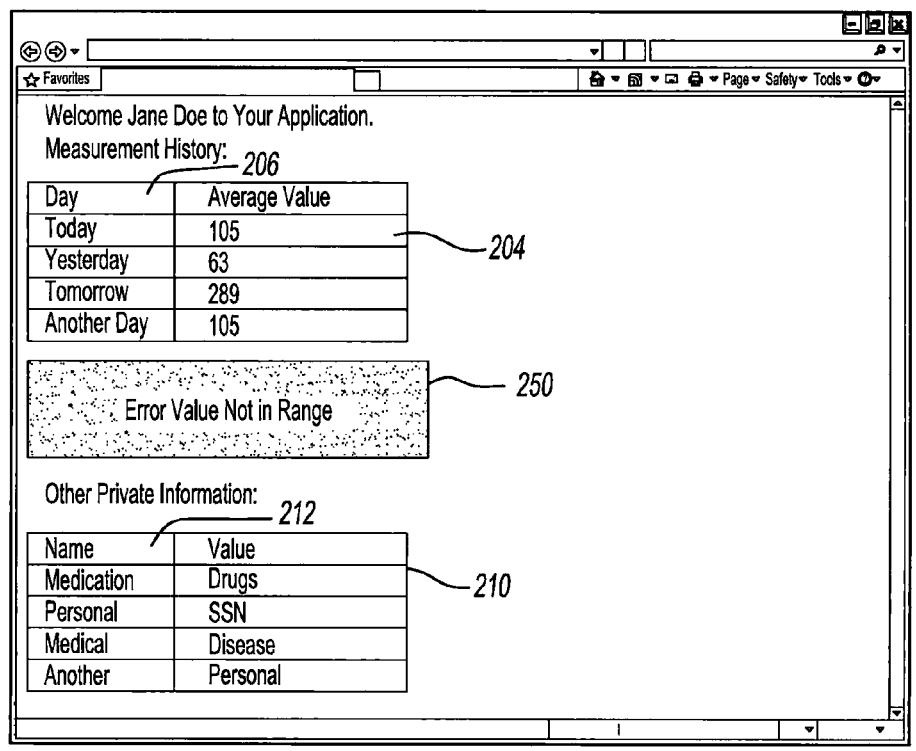
FIG. 3 is an exemplary screen with an error message as seen by a user.

The user can access the web service 102 and the health management application 104 using a personal user account and login (authentication) credentials that include a unique user name "myusername' and a unique password "myuserpassword" associated with the unique user name. The authentication credentials may also include an anatomic feature, such as iris or fingerprint, for example. During an interactive session between the user 10 and the health management application 104, 16 or 18, an error message 250 may be displayed on electronic screen 20 or 24. For example, the error message 250 may appear in the context of an electronic file or browser tab or form 200 ("electronic form 200") that displays a measurement history of the patient, such as, for example, in the form of a table with bG values (or other private health values) 204 by corresponding dates (or non-personal, non-private entries) 206, as shown in FIG. 3. In addition to the measurement history, the electronic form 200 may display other personal and/or private information 210 of the patient, such as full name, social security number, health insurance information and identification or contract number, list of medications, various medical conditions, health history and other non-private information corresponding to standard (non-personal) field names 212.

The error message 250 may relate to a missing value, an out-of-range value, a failure to properly display the electronic form 200, a formatting error in a table or text of the electronic form 200, a failure to retrieve and display the electronic form 200 or in tools or functions or other options associated with the electronic form 200. The user 10 may have access to a help menu from the HMA 104 or the web service 102, but unless simple procedures such as re-booting or automated diagnostic procedure can resolve the error, the user 10 generally places a call (by land or cellular phone or internet or digital phone service) to contact a customer support service 50 associated with the health management application 104 (16, 18) and reaches a support person 52. The support person 52 has a support account with the web service 102 and the health management application 104 that includes login (authentication) credentials with a unique user name "mysupportname' and a unique password "mysupportpassword" associated with the unique support name. The support person's authentication credentials may also include an anatomic feature, such as iris and fingerprint, for example. In some cases, the support person 52 may be able to provide help without access to the user's screen by merely logging into the support account with the support person's own credentials and attempting to replicate the user's actions as described by the user 10 during the call without having access to the user's electronic screen 20, 24 or the user's account. In many cases, however, it is more efficient or even necessary for the support person 52 to see what the user 10 sees during a session that resulted in the error message 250. As the availability of different operating systems, applications, versions and devices that can be used interactively has significantly increased, it may not be cost-effective and or time-efficient, both for the user 10 and for the support person 52 to attempt to recreate the user's session independently by accessing corresponding versions, devices and software that the user 10 may be currently operating.

When the user 10 calls the customer support service 50, the support person 52 may ask and receive the user's permission to access the user's account and to see and/or recreate the session with the user's credentials. The request and authorization, as well as additional data, can be recorded in an audit log 160 to satisfy the HIPAA or other governmental regulations with various additional requirement or safeguards, such as, for example, that the support person 52 is already trained to respect the user's private data and work according to requirements and spirit of HIPAA.

In contrast, the present teachings allow the support person 52 to access the user's account and replicate the session that resulted in the error message without being able to see any private or protected data of the user 10. Specifically, and referring to FIGS. 1 and 2, the support person 52 can access the web service 102 and the HMA 104 and/or a support application 106 from a customer support PC or other computer processing device 54 having an electronic screen display 56 via a communications network 40 using the support person's authentication credentials and partial authentication information from the user 10, such that the support person cannot obtain full access to the user's session from the partial user credentials. For example, the support person can authenticate for accessing a redacted version of the user's account by using the support person's own password "mysupportpassword" and a linked user-support unique name that links the unique name of the user 10 and the unique name of the support person 52 by a predetermined linking rule. The linked user-support name can be verified by a software module of the system 100, such as an authentication service 150 that communicates or is part of the web service 102 of the system 100. When the support person 52 is authenticated with the linked user-support password, the support person can send requests for access to the user's account in the health management application 104 as the user 10, but any information received back from the user's account with the health management application 104 must pass through a redaction module 108 before it is sent to the support application 106 from which the support person can retrieve it in his processing device 54.

Figure 2:
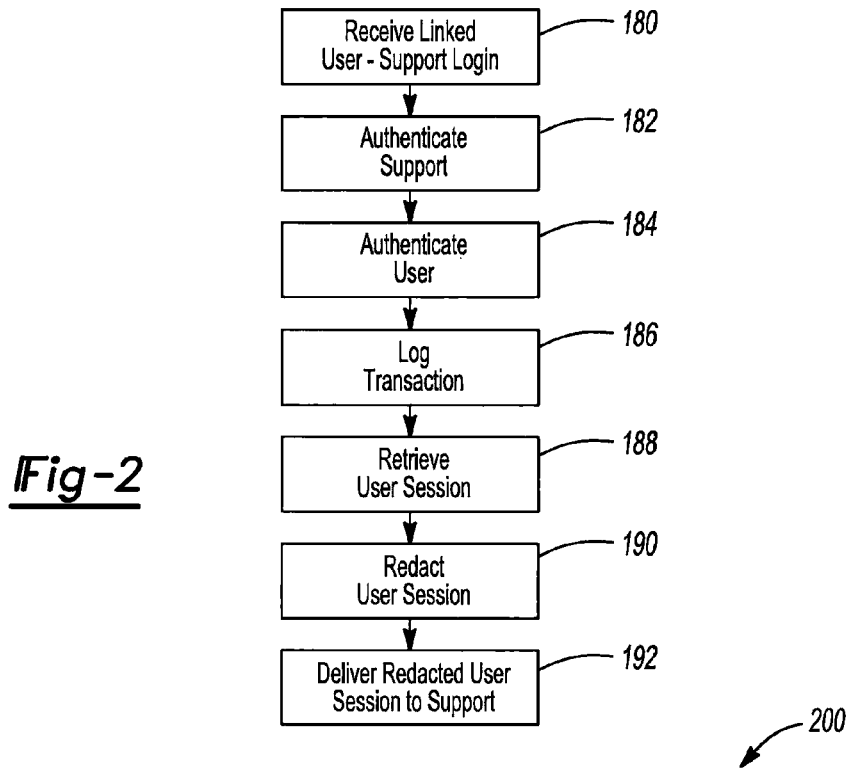
FIG. 2 is an exemplary flow chart for a support session.
Figure 4:
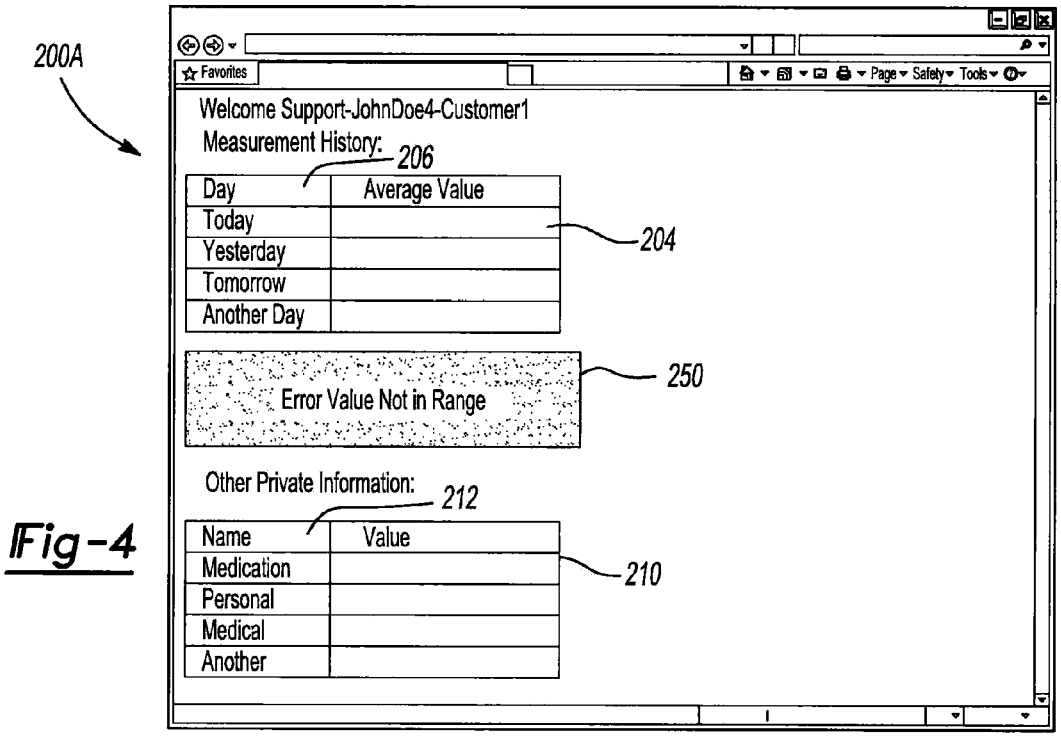
FIG. 4 is a redacted version of the screen of FIG. 3 as seen by a support person.

According to the present teachings, the support person 52 first requests permission to access the user's account with access to see the user's electronic screen or session with the error message 250, but without access to any protected private data or other information, using only the user's unique name and not the user's unique password. This request and permission received by the user 10 can be recorded in the audit log 160 or other module communicating with web service 102 and the support application 106. The support person 52 can log into the web service 102 using the linked user-support unique name, according to the linking rule, and the support's person own password. Referring to FIG. 2, when the authentication service 150 receives the linked user-support login at 180, the authentication service 150 can use the linking rule, parse the linked user-support unique name and authenticate the support person 52 at 182 and the user at 184. The authentication service 150 can then log the transaction at 186 in the audit log 160 and connect the support person 52 to the support application 106. The support application 106 can access the user's account in the health management module but only allows the support person 52 to retrieve the user's session or replicate the user's session from HMA 104 after sanitizing the user's session in the redaction module 108. Specifically, when the support person 52 is authenticated with the linked user-support credentials, the support application 106 allows unrestricted one-way access to the user's account in the health management application 104, but any return response must pass through the redaction module before it can be sent to the support person's processing device 54 via the communications network 40 (or other communications network). The redaction module 108 retrieves the user's session in an electronic file form at block 188 and redacts private information according to instructions and rules programmed in the redaction module 108, at block 190. For example, in one embodiment, the fields of the health management application 104 that correspond to private or otherwise protected information can be already tagged in the software of the HMA 104. The redaction module 108 searches for tagged fields and nulls or blocks their content to create a redacted electronic file, from which a redacted session is delivered to the display 56 of the support person 52, at block 192. In this respect, the redacted session will display a redacted form 200A in which only the personal or private values or entries 204 and 210 have been removed, as shown in FIG. 4. In some embodiments, the electronic file can be in html (HyperText Markup Language) or other hypertext language or any other language that can be read by a web browser and converted to visible or audible content in a web page. In other embodiments, the electronic file can be associated with a particular application, such as the health management application, and can be in any other language associated with the application, including languages used in mobile devices, such as smartphones and tablets, such as Objective-C, C, C++, JavaScript, Adobe Flash Builder, etc.

Figure 5:
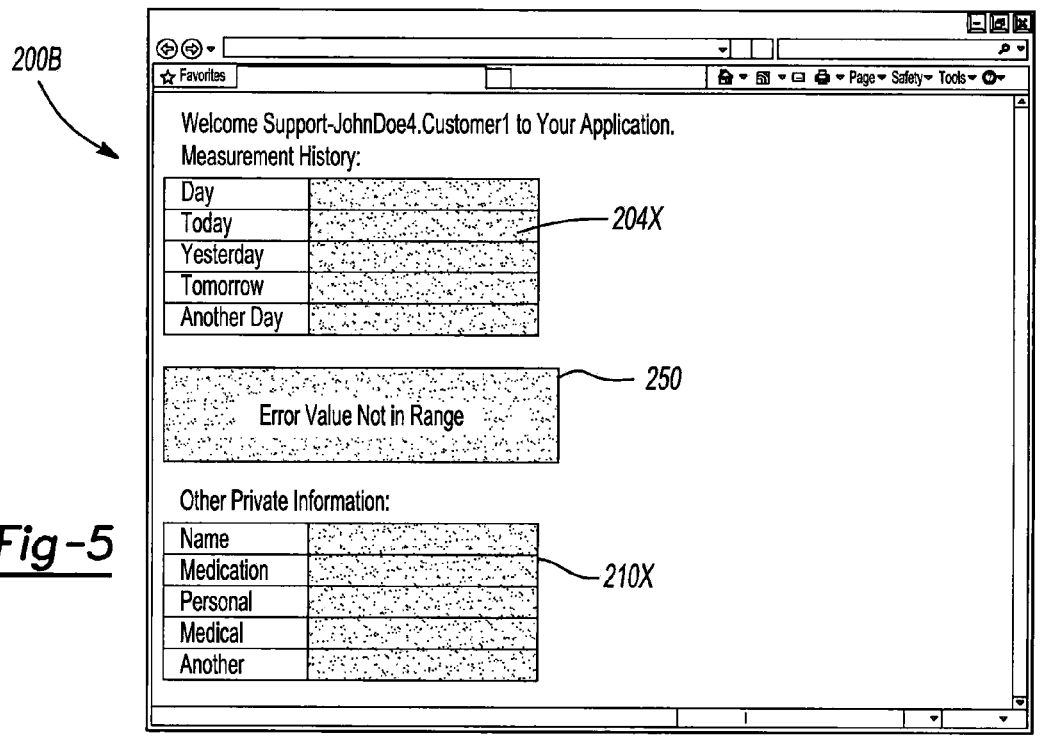
FIG. 5 is another redacted version of the screen of FIG. 3 as seen by a support person.

In another embodiment, the same procedure can be followed, but instead of tagging individual fields that contain private data, entire areas in which private data can be found are pre-tagged for redaction. In this respect, the redacted session will display a redacted form 200B, as shown in FIG. 5, in which areas around private values 204 and 210 appeared blocked as 204X, 210X.

While the user 10 and the support person 52 communicate via a telephone or cellular line, the support person 52 can retrieve dynamically not only the screen page with the error in redacted form, but can also retrace the user's entire session and correct the error in real time without accessing any private information of the user 10.

Because the support person 52 is automatically blocked from seeing any private data of the user 10, and an audit trail can be created in the audit log 160 for accessing the user's account, mitigation and compliance efforts regarding the requirements of HIPAA or other privacy requirements can be reduced.

The linking rule for accessing the user's account after redaction or sanitization can be a concatenation rule in the form of a string that invokes a sanitization or redaction command and also includes the unique names of the user 10 and the support member 52. For example, using the unique names discussed above, a linked user-support name can be "redact-mysupportname.myusername" or "support-mysupportname.mysername". The prefix "redact" or "support" before the symbol "-" can function as a notification of the origin of the request. Accordingly, the authentication service 150 and the support application 106 are instructed to process any requests by the support person 52 via the redaction module 108 and returned only redacted information to the support person 52.

For example, if the user's account name is Jane Doe and her authentication unique name Customer1, and the support person's account name is John Doe and his authentication unique name is JohnDoe4, then the linked unique name can be support-JohnDoe4.Customer1, as seen in FIGS. 4 and 5. In this case, the prefix "support" notifies the authentication service 150 that the request originated from a support person 52 and triggers the operation of the redaction module 108. Generally, any prefix can be used as a trigger followed by a concatenation of the unique names of the support person 52 and the user 10 in a preselected order. The trigger (prefix) can be identified as a string preceding a selected separator symbol:

[trigger] [separator] [support unique name] [user unique name] or

[trigger] [separator] [user unique name] [support unique name]

Summarizing, the present teachings provide a system 100 and method for sanitizing a user's session with a health management application before allowing a support person to access a view of the user's session. Sanitization includes redacting an electronic file of the user's session to remove fields that are pre-tagged as containing sensitive, private or personal information that should be protected or otherwise not disclosed to other parties without consent of the user.

The support person 52 can access the user's redacted session dynamically to view what is currently displayed on the user's electronic screen 20 or 24 with all the sensitive information redacted, such as nulled, removed, blocked, obscured, etc. To obtain such restricted access to the user's account, the support person 52 logs into the web service 102 using the support person's own password but a linked user-support name that is provided by the support person using a predetermined and preprogrammed linking rule. The linking rule includes a notification prefix and a string concatenating the authentication names of the support person and the user. The notification prefix can function as a command or trigger for the operation of the redaction module 108.

Although the various modules and applications of the system 100 are shown in particular locations or associations in FIG. 1, these locations are merely exemplary. For example, the redaction module 108 can reside in the support application 106 or be a separate module that communicates with the other modules of the system 100. Similarly, the user and support data can be located in the authentication service 150 or in a separate database that can be accessed by the authentication service 150.

The authentication service 150 can include or can access various user lists and support person lists. The user lists may additionally include different categories of users, such as patients, clinicians, as well as groupings by geography or particular health care management applications. Similarly, the support lists may include groupings by geography, type of support, such as patient applications, clinician applications, technical level and expertise or other characteristics. In some cases, an additional level of authentication or authorization may be included, i.e., matching a user belonging to a group A only to support persons belonging to group C and not to support persons belonging to group B, for example. This filtering may also be implemented by an automated answering agent that directs a call from a user of group A to a support person belonging in a recommended group C, for example.

As used herein, the phrase at least one of A, B, and C should be construed to mean a logical (A or B or C), using a non-exclusive logical or. It should be understood that steps within a method may be executed in different order without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer-readable medium. The computer programs may also include stored data. Non-limiting examples of the non-transitory tangible computer readable medium are nonvolatile memory, magnetic storage, and optical storage.

The broad teachings of the disclosure can be implemented in a variety of forms. Therefore, while this disclosure includes particular examples, the scope of the disclosure should not be so limited since other modifications will become apparent to the skilled practitioner upon a study of the drawings, the specification, and the following claims.

What is claimed is:

1. A method for accessing a user's account by customer support without viewing the user's private data, the method comprising:
   receiving, in an application module communicating with a web service, a request for authentication by a support person using a linked user-support login name that includes a concatenation of the support person's login name, the user's login name and a prefix;
   authenticating the user, by the application, using the user's login name extracted from the linked user-support login name;
   authenticating the support person, by the application, using the support person's login name extracted from the linked user-support login name;
   retrieving, by the application, a current user session as viewed by the user on an electronic screen of a processing device of the user, the retrieval being performed in response to the authentication of the user and the support person;
   dynamically redacting private data of the user from the user session to create a redacted user session, where the prefix acts as a trigger for activating a redaction module for redacting the user's current session; and
   delivering the redacted user session for display in an electronic screen of a processing device of the support person.

2. The method of claim 1, further comprising:
   recording in an audit log the request of authentication by the support person.

3. The method or claim 1, wherein the linked user-support login name is a string including a prefix as a trigger for activating a redaction module for redacting the user's current session.

4. The method of claim 3, wherein the authentication credentials of the support person include the support person's unique password.

5. The method of claim 4, wherein the prefix and the concatenation are separated by a symbol.

6. The method of claim 1, wherein the request of authentication by the support person using the linked user-support login includes the support person's anatomic authentication credentials for the application module.

7. The method of claim 1, wherein dynamically redacting the user session includes dynamically redacting private information of the user.

8. The method of claim 7, wherein redacting private information includes identifying fields pre-tagged as private in an electronic file of the user's current session and redacting values associated with the pre-tagged fields.

9. The method of claim 7, wherein redacting private information includes identifying areas pre-tagged as private in an electronic file of the user's current session and redacting the pre-tagged areas.

10. The method of claim 7, wherein the application module is a health management module.

11. The method of claim 7, wherein the application module is a management module for diabetes care.

12. The method of claim 1, wherein the current session of the user displays an error message from the application module in the electronic screen of the user.

13. A method for accessing a user's account by customer support without viewing the user's private data, the method comprising:
   receiving, in a health management module communicating with a web service, a request for authentication by a support person, wherein the request includes a user-support login string that concatenates a notification prefix with a user's login name with a support person's login name, along with the support person's password for the health management module;
   parsing, by the health management module, the user-support login string;
   authenticating, by the health management module, the user using the user's login name extracted from the user-support login string, wherein in response to the user-support login string having the notification prefix, the method further comprises:
   authenticating, by the health management module, the support person using the support person's login name extracted from the user-support login string;
   retrieving a current session of the user as viewed by the user in an electronic screen of a processing device of the user;
   identifying in an electronic file of the current session of the user fields pre-tagged as private;
   dynamically redacting values of the pre-tagged fields to create a redacted electronic file for a redacted user session;

sending the redacted electronic file to a support module of the web service; and displaying the redacted user session in an electronic screen of a processing device of the authenticated support person based on the redacted electronic file.

14. The method of claim 13, further comprising:
recording in an audit log the request of authentication by the support person.

15. The method of claim 13, wherein the health management module is a diabetes care module.

16. The method of claim 1, wherein the current session of the user displays an error message from the health management module in the electronic screen of the user.

17. A system for accessing a user's account by customer support without viewing the user's private data, the system comprising:
a web service;
a health management module communicating with the web service and accessible by a user having an account and authentication credentials with the web service;
a support module communicating with the web service and accessible by a support person having a support account and authentication credentials with the web service;
an authentication service communicating with the web service and programmed to:
(a) authenticate the user with the user's authentication credentials;
(b) authenticate the support person with the support person's authentication credentials; and
(c) authenticate the support person with linked user-support credentials for a limited access of the user's account, wherein the linked user-support credentials include a concatenation of the user's credentials, the support person's credentials and a prefix; and a redaction module communicating with the authentication service and programmed, in response to the prefix, to dynamically redact private data from a user's session with the web service and send the redacted user session to the support module for access by the support person, when the support person and the user are authenticated with the linked user-support credentials, wherein the prefix serves as a trigger for activating the redaction module.

18. The system of claim 17, further comprising an audit log for logging a request for linked user-support authentication.

19. The system of claim 17, wherein the redaction module is programmed to redact portions of the user's session that are pre-tagged for redaction in an electronic file of the current session prior to providing access to the support person.

20. The system of claim 19, wherein the user's current session includes an error message.

* * * * *